United States Patent
Misirian

(10) Patent No.: US 10,633,317 B2
(45) Date of Patent: Apr. 28, 2020

(54) METHOD OF PRODUCTION OF METHANOL USING $CO_2$ AND $H_2$

(71) Applicant: Hagop Jake Misirian, Santa Ana, CA (US)

(72) Inventor: Hagop Jake Misirian, Santa Ana, CA (US)

( * ) Notice: Subject to any disclaimer, the term of this patent is extended or adjusted under 35 U.S.C. 154(b) by 0 days.

(21) Appl. No.: 15/488,844

(22) Filed: Apr. 17, 2017

(65) Prior Publication Data
US 2018/0297921 A1  Oct. 18, 2018

(51) Int. Cl.
*C07C 29/00* (2006.01)
*C07C 31/00* (2006.01)
*C07C 31/04* (2006.01)
*C07C 29/151* (2006.01)

(52) U.S. Cl.
CPC .......... *C07C 31/04* (2013.01); *C07C 29/1512* (2013.01); *C07C 29/1518* (2013.01)

(58) Field of Classification Search
CPC ............................ C07C 31/04; C07C 29/1518
USPC ....................................................... 568/913
See application file for complete search history.

(56) References Cited

U.S. PATENT DOCUMENTS

| | | | | |
|---|---|---|---|---|
| 5,631,302 A | * | 5/1997 | Konig | ................... B01J 8/0488 252/373 |
| 6,875,794 B2 | * | 4/2005 | Seiki | ................... C07C 29/1518 518/700 |

* cited by examiner

*Primary Examiner* — Sikarl A Witherspoon

(57) ABSTRACT

Utilizing the common knowledge formula for creation of methanol $CO_2+3H_2 \rightarrow CH_3OH+H_2O$; for each mole of carbon dioxide, three moles of hydrogen are needed to produce one equivalent unit of methanol.

Figure 1:
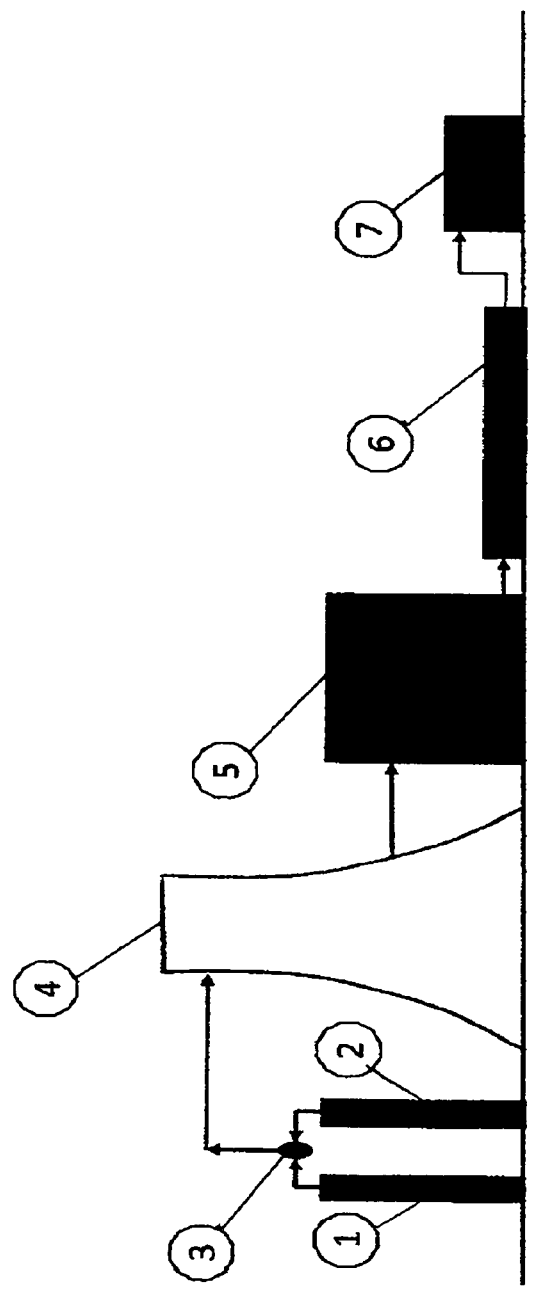
Figure 2:
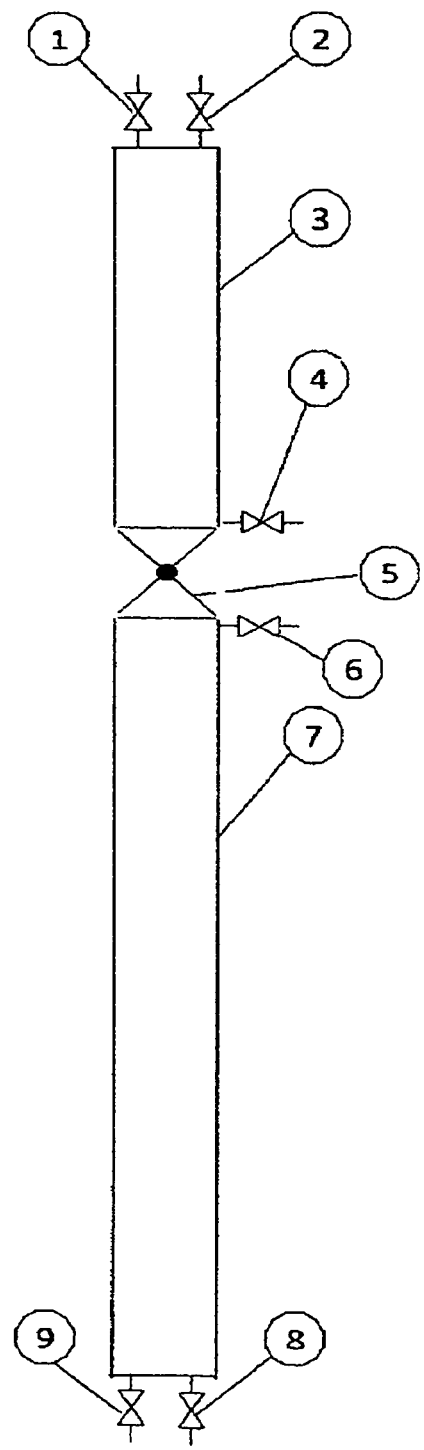

Mixing two gases and producing methanol can be accomplished per the one-line diagram concept, FIG. 1, and gas mixing apparatus, FIG. 2; under high pressure (from 3250 to 5000 psi) and high temperature (750 to 800° F.) without the presence of a catalyst.

The hypothesis in this case is that the closer the mixing temperature is to the auto-ignition of hydrogen, the higher is the quality of the mixing environment. The mixing temperature in my invention is guided by the auto-ignition of hydrogen in this case (auto-ignition for hydrogen is 932° F. (or 500° C.) and the auto-ignition temperature for methanol is 867° F. (or 464° C.).

After mixing the two gases, the result is methanol and water. The first step in this stage is to cool the substance by way of cooling tower, followed by a pressure lowering tank.

Next is a separation process to separate methanol and water. By cooling the substance/mixture about 28.4° F. (−2° C.), the water will freeze, turning into ice, and ice will be removed from methanol mechanically. Water and methanol then will be stored in appropriate tanks (FIG. 1).

2 Claims, 2 Drawing Sheets

METHOD OF PRODUCTION OF METHANOL USING $CO_2$ AND $H_2$

1. INTRODUCTION

I, Hagop Misirian, citizen of the United States of America, residing in the city of Santa Ana, Calif., have invented a new and useful one-line diagram (FIG. 1) concept and gas mixing apparatus (FIG. 2) which will help to achieve mass production of methanol, comprising carbon dioxide ($CO_2$) and hydrogen ($H_2$). Carbon dioxide and hydrogen are produced at a separate location. The produced methanol then can be converted into a hydro-carbon fuel, which is equivalent to regular unleaded gasoline.

The method for production of carbon dioxide to be used in this mass production has been filed as a separate patent (Application title "METHOD OF PRODUCTION OF CARBON DIOXIDE ($CO_2$) USING LIME TO LIMESTONE CHEMICAL REACTION" application Ser. No. 15/483,377) by me (Hagop Misirian).

2. DESCRIPTION

In order to utilize the common knowledge formula for creation of methanol $CO_2+3H_2 \rightarrow CH_3OH+H_2O$ (for each mole of carbon dioxide, three moles of hydrogen needed to produce one equivalent unit of methanol); the one-line diagram shall be followed per FIG. 1. First, supply tanks (Item-1 and Item-2 in FIG. 1; which consist of 14-inch diameter, 80 schedule stainless steel pipes, 25 feet high, wrapped around with electrical heating coils. Renewable electrical power source will be used in this case) shall be pressurized as follows: for the hydrogen ($H_2$), Item-2 in FIG. 1, the inside air shall be replaced with the hydrogen first. Hydrogen shall be loaded from the top of the tank. Due to the reason that hydrogen is lighter than air, hydrogen will stay on top. By continuous, gradual loading, the air will be replaced completely with hydrogen. Next, the air drainage valve (at the lower elevation of the tank) shall be closed and continue pressurizing about 3250 psi. After pressurizing is complete, the tank shall be heated about 750° F. (398.9° Celsius or 672° Kelvin).

Loading carbon dioxide ($CO_2$) into the supply tank, Item-1 in FIG. 1, can be accomplished the opposite way, due to the reason that carbon dioxide is heavier than air. Pressurizing and heating can be accomplished same way as the hydrogen supply tank. Supply tanks Item-1 and Item-2 in FIG. 1 are connected to a mixing chamber apparatus.

The mixing chamber apparatus (Item-3 in FIG. 1 and also detailed in FIG. 2) operates as follows. First, for each unit volume of carbon dioxide ($CO_2$), the appropriate volume of hydrogen ($H_2$) shall be determined for the mixing process (for each mole of carbon dioxide, three moles of hydrogen). In this case, six-inch diameter 80 schedule stainless steel pipe is used. By applying the Ideal Gas Law and then the Universal Gas Law (the volume of the gas is directly proportional to the number of molecules of gas if temperature and pressure are kept constant) for two feet long pipe volume of carbon dioxide ($CO_2$), appropriate volume of hydrogen ($H_2$) is calculated. Per FIG. 2, for carbon dioxide ($CO_2$), 80 schedule six inches diameter and two feet long stainless-steel pipe (Item-3), appropriate volume or length of the pipe for hydrogen ($H_2$) is equal to two feet multiplying with multiplier of 3.01. In FIG. 2, the depicted mixing chamber consists of a 2-feet long (Item-3 in FIG. 2) and 6.02 feet long pipe (Item-7 in FIG. 2), connected with six-inch diameter gate valve (Item-5 in FIG. 2).

Prior loading the gases in to the mixing chamber, the inside air shall be replaced with carbon dioxide ($CO_2$) and hydrogen ($H_2$). Item-5 in FIG. 2, the six-inch diameter gate valve is closed; at the same time, Item-4 in FIG. 1 (carbon dioxide ($CO_2$) initial loading valve) and Item-1 in FIG. 2, is opened. Item-2 in FIG. 2 is an air drainage valve. Item-1 in FIG. 2 is closed at this time. Gradually the inside air will be replaced with $CO_2$. When air Is removed, Item-2 and Item-4 in FIG. 1 is closed and Item-3 in FIG. 2 is loaded with $CO_2$ about 3250 psi from Item-1 valve in FIG. 2. Next, replacing air with hydrogen ($H_2$), Item-5 in FIG. 2, the six-inch diameter gate valve and Item-9 in FIG. 2 close. Item-6 and Item-8 in FIG. 1 are open.

When air removal is complete, Item-8, air drainage valve in FIG. 2 is closed. After loading completion with hydrogen ($H_2$), the mixing chamber is ready for the mixing reaction (all valves are closed at this stage). At this time, Item-5 in FIG. 2, the six-inch diameter gate valve, will be opened. Subsequently, the two pipes will convert into one continues pipe, with carbon dioxide ($CO_2$) on top and hydrogen ($H_2$) below. Natural mixing will follow due to gravitational difference, as carbon dioxide ($CO_2$) will move down and hydrogen ($H_2$) will move up. The duration of mixing is about 30 seconds. After the mixing is completed, Item-9 valve in FIG. 2 opens and the newly created substances (methanol and water) discharged from the mixing chamber.

Prior reloading a mixing chamber, following shall be completed. Item-3 in FIG. 7 shall be replaced with carbon dioxide ($CO_2$) from Item-1 valve and then close Item-5 in FIG. 1 (gate valve); continue pressurizing. Next, prior to closing Item-9 in FIG. 2, hydrogen ($H_2$) shall be reload in the Item-7 from Item-6 valve, gradually pushing down residual created substances (methanol and water) and then close the Item 9 valve in FIG. 1; continue pressurizing. The same loading and discharging will be repeated continuously.

From the mixing chamber, the discharged substance will move to Item-4 in FIG. 1 (cooling tower) and then Item-5 in FIG. 1 (pressure lowering tank about 2 psi).

Next, Item-6 in FIG. 1, a methanol and water separation tank, has a temperature of about 28° F. (2° C.), where water will convert into ice and be removed from methanol mechanically. Water and methanol then will be stored in appropriate tanks Item-7 in FIG. 1.

EXAMPLE

Calculation for a length of the pipe for a carbon dioxide ($CO_2$) and a hydrogen ($H_2$) of mixing apparatus under a same temperature and pressure.

First, define volume for the carbon dioxide ($CO_2$). Used piping in this case is 80 schedule stainless steel for the two gases. Pipe diameter shall be the same for two gases. Due to the reason that mixing apparatus valve opens and closes about every fifteen to thirty seconds, valve operational life expectancy is an issue and smaller diameter valves will last longer. Next, define a diameter and length for the carbon dioxide ($CO_2$) and volume. For an optimum mixing result, a length for the carbon dioxide ($CO_2$) pipe may have to be same as inside diameter of the chosen pipe. In this stage, it is possible to calculate volume for the carbon dioxide ($CO_2$). Per the following formula; $CO_2+3H_2 \rightarrow CH_3OH+H_2O$ for each mole of carbon dioxide and three mules of hydrogen; calculate the moles of carbon dioxide (COD) in this volume under same pressure and temperature.

By applying the Ideal Gas Law and then the Universal Gas Law (the volume of the gas is directly proportional to the number of molecules of gas it temperature and pressure are kept constant).

$$PV=nRT \text{ subsequently } n=PV/RT$$

where
P is pressure
V is volume
n is the number of moles
R is the universal gas constant
T is temperature After calculating number of molecules (n) in carbon dioxide ($CO_2$), subsequently (n) for the hydrogen (H2) is three times more.

When (n) is plugged in for hydrogen (H2); V=nRT/P, (V) volume for hydrogen (H2) and length for the hydrogen (H2) pipe can be calculated.

4. LIST OF FIGURES AND BRIEF DESCRIPTION

FIG. 1: Diagram Outlining Production Plant (one-line diagram)

Item-1 and Item-2, supply tanks for hydrogen and carbon dioxide gas. They are 14-inch diameter, 80 schedule stainless steel pipes, and are 25 feet high, wrapped around with electrical heating coils.

Item-3, mixing chamber, where the reaction between hydrogen gas and carbon dioxide gas takes place Item-4 depicts the cooling tower Item-5 depicts the pressure reduction tank Item-6 depicts a separation tank for methanol and water with operating temperature of −2° C.

Item-7 depicts two separate storage tanks for methanol and water

FIG. 2: Diagram of the Mixing Chamber with detail

Item-1 depicts a valve for the $CO_2$ supply line

Item-2 depicts an air drainage valve only

Item-3 depicts an 80 schedule, 6-inch diameter, 2-feet long stainless-steel pipe Item-4 depicts a valve from the $CO_2$ tank at the time of the replacement of air with $CO_2$ Item-5 depicts a 6-inch diameter gate valve Item-6 depicts a loading valve for hydrogen Item-7 depicts an 80 schedule, 6-inch diameter, 6.02-feet long stainless-steel pipe Item-8 depicts the air drainage valve to replace air with hydrogen Item-9 depicts the drainage valve for the newly created products (methanol and water) of the chemical reaction

5. SUMMARY OF THE INVENTION

This method does not need a catalyst and does not create leftover byproducts.

Using this fuel for internal combustion engines will have zero impact to the environment. It works as follows: Assuming hydrogen is created via electrolysis (water and electricity) and carbon dioxide ($CO_2$) is removed from the air. At the time of fuel combustion, carbon dioxide ($CO_2$) will be released back to the atmosphere. Hydrogen ($H_2$) is created by electrolysis and oxygen is released to the atmosphere. At the time of the fuel usage, oxygen will be used for combustion, creating zero impact to the environment.

Optimum pressure and temperature for mixing hydrogen and carbon dioxide gases are unknown at this time. Additionally, for the mixing chamber apparatus, optimum geometric dimensions are unknown.

The invention claimed is:

1. A method for the continuous mass production of methanol from carbon dioxide and hydrogen in absence of catalyst, comprising loading hydrogen to the top of a first supply tank that consist of 14-inch diameter, 25 feet high stainless steel pipes wrapped with electrical heating coils and equipped with an air drainage valve at the lowest level of the tank, wherein air is completely replaced by continuous and gradual loading of hydrogen; closing the air drainage valve and pressurize to about 3250 psi; heating the tank to about 7500 F; loading the bottom of a second supply tank with carbon dioxide and then heating and pressurizing in the same manner as the hydrogen supply tank; sending carbon dioxide and hydrogen to a mixing chamber to be reacted, thereby producing methanol and water; from the mixing chamber, sending methanol and water to a cooling tower, followed by a pressure lowering tank operated at less than 2 psi of pressure; sending the methanol and water to a separation tank, wherein about 28° F., frozen water is separated from methanol, and separated water and methanol are stored in appropriate tanks.

2. A mixing chamber apparatus for the continuous mass production of methanol according to claim 1, said mixing chamber comprising an upper portion, comprising a 2 ft long pipe for a carbon dioxide connected to a six-inch diameter gate valve; for hydrogen, a 6.02 ft long pipe connected with gate valve, wherein mixing chamber assembly is positioned perpendicular to the horizon; wherein pipes for carbon dioxide and hydrogen are connected via gate valve and then to carbon dioxide and hydrogen supply tanks, respectively; said mixing chamber comprising air drainage and mix-chamber drainage valves.

* * * * *